United States Patent
Rossi

(10) Patent No.: US 11,246,546 B2
(45) Date of Patent: Feb. 15, 2022

(54) COLLIMATOR AND RADIOLOGICAL EQUIPMENT

(71) Applicant: GENERAL MEDICAL MERATE S.P.A., Seriate (IT)

(72) Inventor: Ivano Rossi, Seriate (IT)

(73) Assignee: GENERAL MEDICAL MERATE S.P.A., Seriate (IT)

( * ) Notice: Subject to any disclaimer, the term of this patent is extended or adjusted under 35 U.S.C. 154(b) by 65 days.

(21) Appl. No.: 16/608,575

(22) PCT Filed: Apr. 27, 2018

(86) PCT No.: PCT/IB2018/052945
§ 371 (c)(1),
(2) Date: Oct. 25, 2019

(87) PCT Pub. No.: WO2018/198089
PCT Pub. Date: Nov. 1, 2018

(65) Prior Publication Data
US 2020/0178912 A1    Jun. 11, 2020

(30) Foreign Application Priority Data
Apr. 28, 2017    (IT) .................. 102017000046573

(51) Int. Cl.
| G21K 1/02 | (2006.01) |
|---|---|
| A61B 6/06 | (2006.01) |
| A61B 6/10 | (2006.01) |
| A61B 6/00 | (2006.01) |

(52) U.S. Cl.
CPC ................ *A61B 6/06* (2013.01); *A61B 6/107* (2013.01); *A61B 6/40* (2013.01)

(58) Field of Classification Search
CPC .. G01N 2035/00326; A61B 6/06; A61B 6/08; A61B 6/54; A61N 5/1045; G02B 27/09; G02B 27/0916; G02B 27/0933; G02B 27/0988; G21K 1/02; G21K 1/025; G21K 1/04; G21K 1/043; G21K 1/046
See application file for complete search history.

(56) References Cited

U.S. PATENT DOCUMENTS

| 4,179,100 A | 12/1979 | Sashin et al. | |
|---|---|---|---|
| 2006/0023842 A1* | 2/2006 | Sohal | G21K 1/04 378/147 |
| 2008/0023636 A1 | 1/2008 | Chowdhury et al. | |
| 2012/0275560 A1 | 11/2012 | Demianovich | |
| 2013/0044860 A1* | 2/2013 | Nicholson | G21K 1/04 378/62 |

(Continued)

FOREIGN PATENT DOCUMENTS

DE    102007028231 A1    1/2009

OTHER PUBLICATIONS

English machine translation of DE102007028231.

*Primary Examiner* — Don K Wong
(74) *Attorney, Agent, or Firm* — Dickinson Wright PLLC; Andrew D. Dorisio

(57) ABSTRACT

The collimator (3) for a radiological equipment (1) comprises shielding means (6, 7, 9, 10, 11) made of tungsten-based radiation-absorbent plastic material; such means may be proximal radiated field closure elements and/or radiated field propagation elements; such means comprise at least one radiated radiogenic field propagation element (6).

20 Claims, 2 Drawing Sheets

(56) References Cited

U.S. PATENT DOCUMENTS

| | | |
|---|---|---|
| 2013/0058462 A1 | 3/2013 | Jenkins et al. |
| 2013/0177131 A1 | 7/2013 | Teng |
| 2014/0169533 A1* | 6/2014 | Razzano .................. A61B 6/14 |
| | | 378/205 |
| 2016/0135767 A1* | 5/2016 | Kim ....................... G03B 21/28 |
| | | 378/63 |

* cited by examiner

COLLIMATOR AND RADIOLOGICAL EQUIPMENT

FIELD OF THE INVENTION

The present invention concerns a collimator and radiological equipment.

BACKGROUND

Radiological equipment, in particular for medical use, requires shielding means for absorbing all the radiation that is not used for obtaining the image of the patient.

Lead-based plates are commonly used for that purpose. Such plates are placed at the outer walls of the casing of the collimator of the equipment.

From patent documents DE102007028231A1 and U.S. 20130177131 collimators are known in which at the outer walls of the box-shaped casing of the collimator shielding plates are placed made of a tungsten-based plastic composite; in practice, these solutions are limited to replacing lead-based material with a tungsten-based plastic material. Also, particularly the solution according to U.S. 20130177131 was designed for computerised tomography equipment.

SUMMARY

The general purpose of the present invention is that of shielding without using lead-based material.

Radiation-absorbent material exist that do not contain lead, however their cost per unit of weight is high and it would therefore be too expensive to produce the perimeter shielding slabs using such alternative materials, as indicated in patent documents DE102007028231A1 and U.S. 20130177131.

A more specific object of the present invention is therefore that of shielding through such alternative materials without any particular increase in cost.

The Applicant has concentrated in particular on solutions suitable for conventional radiological equipment, i.e. adapted for providing radiographic or radioscopic images.

Such objectives are substantially reached thanks to what is set out in the appended claims that form an integral part of the present description.

The idea underlying the present invention is to realise shielding means made of tungsten-based radiation-absorbent plastic material. More in particular, at least one radiated field propagation element made of tungsten-based radiation-absorbent plastic material is provided; furthermore, advantageously, also radiated field closure elements made of tungsten-based radiation-absorbent plastic material may be provided.

LIST OF FIGURES

Figure 1:
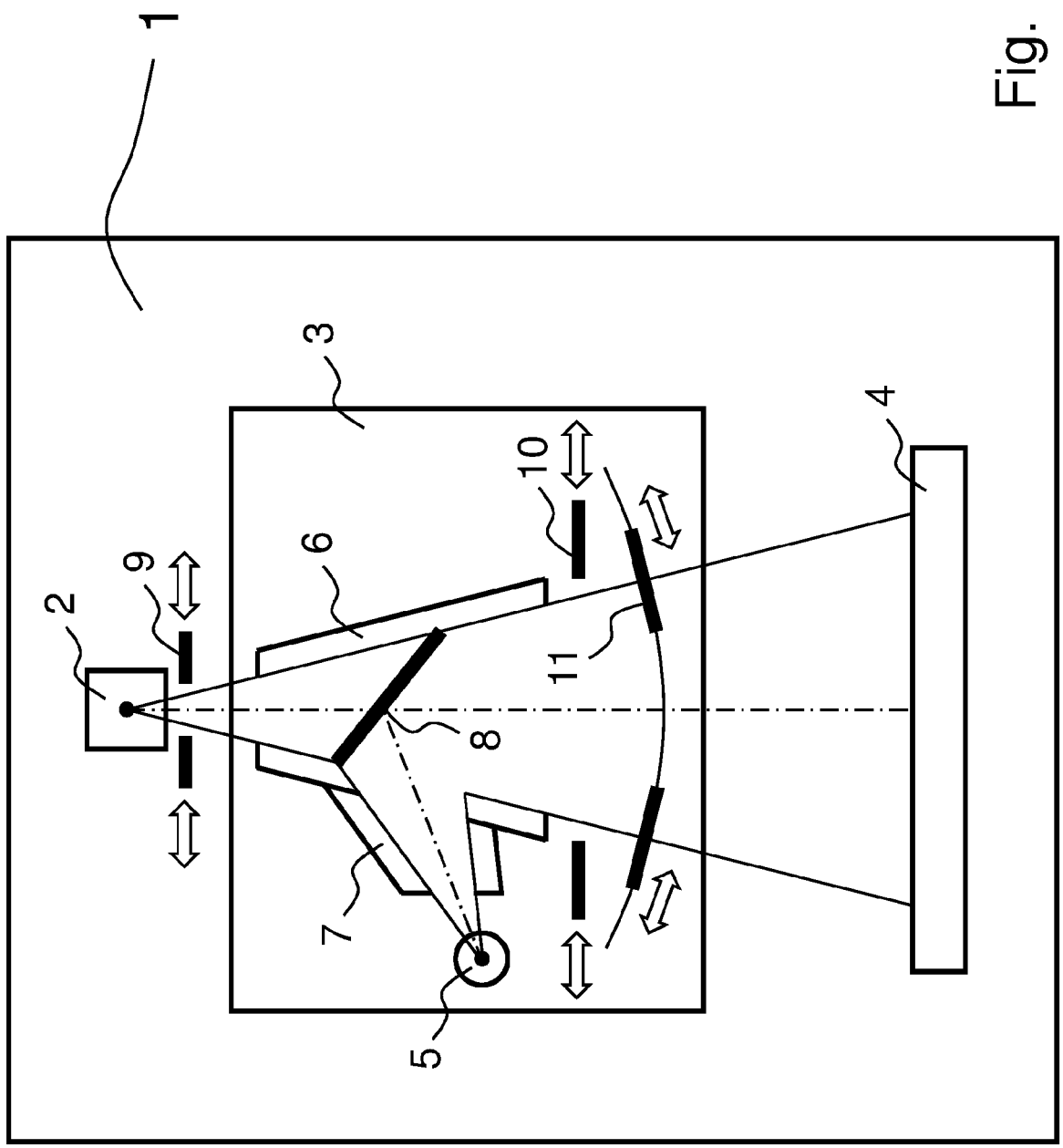
Figure 3:
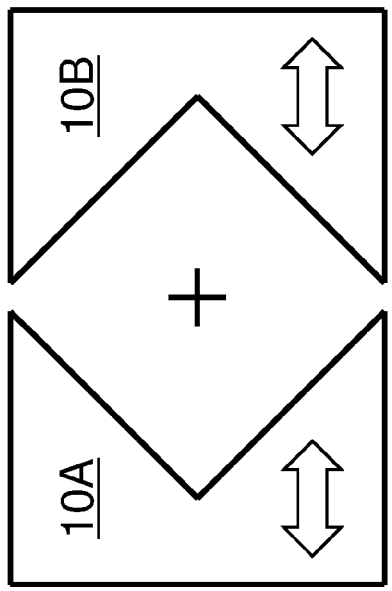
Figure 2:
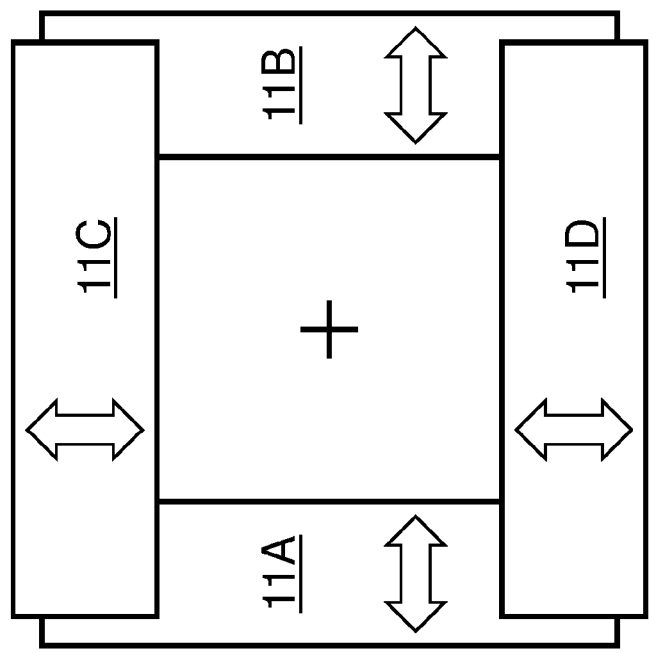

The present invention will become clearer from the following detailed description to be considered together with the appended drawings in which:

FIG. 1 shows a very schematic side view of an embodiment of radiological equipment for medical use, in particular of its collimator, FIG. 2 shows a schematic view from above of distal radiated field closure elements of the collimator of FIG. 1, and FIG. 3 shows a schematic view from above of intermediate radiated field closure elements of the collimator of FIG. 1.

As can be easily understood, there are various ways of practically implementing the present invention which is defined in its main advantageous aspects in the appended claims.

DETAILED DESCRIPTION

A radiological equipment is made of many components; for the purpose of the present invention the collimator is the most significant, i.e. the component that is used to shape the radiated radiogenic field from which the image of the patient is obtained.

In medical radiological equipment, the collimator also generates a radiated light field, having the same shape as the radiated radiogenic field, to understand which will be the image of the patient before radiating the patient.

In FIG. 1, the radiological equipment is indicated with the number 1 and the collimator with number 3; it is, in particular and typically, conventional radiological equipment.

The radiogenic field is generated by a radiogenic tube, indicated with the number 2 in FIG. 1.

In FIG. 1, a patient table 4 is also shown on which a patient (not shown) rests or a part (not shown) of a patient when a test is to be performed, i.e. when an image is to be obtained.

The collimator 3 comprises shielding means (indicated with the numbers 6, 7, 9, 10 and 11 in FIG. 1) made of tungsten-based radiation-absorbent plastic material; in particular, such material contains at least 80% by weight of tungsten; good results can be obtained, for example, with about 90%. Being plastic, such material is suitable for making parts of any shape (in particular different from slab shaped) and of any size (in particular small).

Such means may also be radiated field closure elements and/or radiated field propagation elements. They are relatively small parts with respect to the dimensions of the outer walls of the collimator casing. Furthermore, they are parts that are particularly suitable for intercepting and absorbing diffused radiation.

The shielding means (made of radiation-absorbent plastic material) may comprise proximal radiated field closure elements 9; typically and advantageously there will be four of such elements.

The shielding means (made of radiation-absorbent plastic material) may comprise intermediate radiated field closure elements 10; typically and advantageously there will be two of such elements, as shown in FIG. 3.

The shielding means (made of radiation-absorbent plastic material) may comprise distal radiated field closure elements 11; typically and advantageously there will be four of such elements, as shown in FIG. 2.

The terms "proximal", "intermediate" and "distal" refer to the position with respect to the tube 2, in particular with respect to the focal spot of the tube 2.

It is to be noted that the radiated field closure elements could be a source of diffused radiation and/or intercept diffused radiation.

The shielding means (made of radiation-absorbent material) may comprise a radiated radiogenic field propagation element 6; typically and advantageously, such element is shaped so as to define (preferably exactly) the propagation space of the radiogenic field; more typically and more advantageously, such element has a truncated pyramid shape or a truncated cone shape, preferably a truncated pyramid shape. It can be understood that such element is of rather reduced dimensions with respect to the whole collimator casing.

The shielding means (made of radiation-absorbent material) may comprise a radiated light field propagation element 7; typically and advantageously, such element is shaped so as to define (preferably exactly) the propagation space of the light field; more typically and more advantageously, such element has a truncated pyramid shape or a truncated cone shape, preferably a truncated pyramid shape. It can be understood that such element is of rather reduced dimensions with respect to the whole collimator casing.

Typically and advantageously, according to the present invention, the whole box-shaped collimator casing is made of metal material (e.g. aluminum, iron or steel) and/or plastic material, therefore it is only fairly weakly radiation-absorbent.

Preferably and advantageously, the radiated radiogenic field propagation element 6 and the radiated light field propagation element 7 are integrated into a single part; this part is adapted to house a mirror 8 to reflect the light field generated by a light source 5, in particular a light-emitting diode LED.

It is to be noted that the mirror is a source of diffused radiation that it is best to prevent from propagating in undesired directions precisely through the radiation-absorbent propagation element 6.

The radiated field closure elements 9, 10, 11 are generally movable and/or adjustable.

As can be understood below, the structure, shape and movement of the closure elements is an independent innovation from the structure and shape of the propagation element. These elements preferably have in common the material of which they are made, i.e. tungsten-based radiation-absorbent plastic material.

In the example of FIG. 1, the proximal elements 9 and the distal elements 11 are fixed together so as to move integrally.

In the example of FIG. 1, the distal elements 11 are adapted to move along circular trajectories centred in the focal spot of the radiogenic tube 2.

In particular, it is a first pair of slabs 11A and 11B and a second pair of slabs 11C and 11D, as shown in FIG. 2. The first pair moves synchronously along a first circular trajectory (horizontal in FIG. 2). The second pair moves synchronously along a second circular trajectory (vertical in FIG. 2).

In the example of FIG. 1, there are only two intermediate elements 10, as shown in FIG. 3. They are adapted to move along rectilinear trajectories, in particular synchronously. By appropriately positioning the elements 10 and the elements 11 a conical radiated field is obtained, as though the radiated field closure elements constituted an iris.

It is to be noted that the elements 10 and 11 close both the radiogenic field and the light field.

The invention claimed is:

1. Collimator for a radiological equipment, comprising a shield made of tungsten-based radiation-absorbent plastic material, characterised in that said shield comprises a radiated radiogenic field propagator having a truncated pyramid shape or a truncated cone shape and wherein said shield comprises radiated field closures which are movable or adjustable.

2. Collimator according to claim 1, wherein said radiated radiogenic field propagator is shaped so as to define the propagation space of the radiogenic field.

3. Collimator according to claim 1, wherein said radiated field closures comprise proximal radiated field closures.

4. Collimator according to claim 1, wherein said radiated field closures comprise intermediate radiated field closures.

5. Collimator according to claim 1, wherein said radiated field closures comprise distal radiated field closures.

6. Collimator according to claim 1 wherein said radiated radiogenic field propagator has a truncated pyramid shape.

7. Collimator according to claim 1, wherein said shield comprise a radiated light field propagator.

8. Collimator according to claim 7, wherein said radiated radiogenic field propagator and said radiated light field propagator are integrated in a single part adapted to house a mirror.

9. Collimator according to claim 1, wherein the radiated field closures comprise proximal radiated field closures and distal radiated field closures, and wherein said proximal field closures and said distal field closures are fixed together so as to move integrally.

10. Collimator according to claim 1, wherein the radiated field closures comprise distal radiated field closures, wherein said distal field closures are adapted to move along circular trajectories centered on the focal spot of the radiological equipment.

11. Collimator according to claim 1, wherein the radiated field closures comprise intermediate radiated field closures, wherein said intermediate field closures are adapted to move along rectilinear trajectories.

12. Collimator according to claim 1, comprising a box-shaped casing, wherein said casing is made of metal material and/or plastic material.

13. Radiological equipment comprising a collimator according to claim 1.

14. The collimator of claim 1, wherein the radiated field closures are movable or adjustable with respect to each other.

15. The collimator of claim 1, wherein the radiated field closures are movable or adjustable with respect to the radiated radiogenic field propagator.

16. Collimator for a radiological equipment, comprising distal radiated light or radiogenic field closure elements, wherein said distal radiated light or radiogenic field closure elements are adapted to move along circular trajectories centred on the focal spot of the radiological equipment.

17. Collimator according to claim 16, further comprising proximal radiated light or radiogenic field closure elements, and wherein said proximal radiated light or radiogenic field closure elements and said distal radiated light or radiogenic field closure elements are fixed together so as to move integrally.

18. Collimator according to claim 16, further comprising intermediate radiated light or radiogenic field closure elements, wherein said intermediate radiated light or radiogenic field closure elements are adapted to move along rectilinear trajectories.

19. Collimator according to claim 16, wherein said distal radiated light or radiogenic field closure elements are made of tungsten-based radiation-absorbent plastic material.

20. Radiological equipment comprising a collimator according to claim 16.

* * * * *